United States Patent
Boese et al.

(10) Patent No.: US 7,860,282 B2
(45) Date of Patent: Dec. 28, 2010

(54) METHOD FOR SUPPORTING AN INTERVENTIONAL MEDICAL OPERATION

(75) Inventors: Jan Boese, Eckental (DE); Marcus Pfister, Bubenreuth (DE); Norbert Rahn, Forchheim (DE); Bernhard Sandkamp, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1132 days.

(21) Appl. No.: 11/526,176

(22) Filed: Sep. 22, 2006

(65) Prior Publication Data

US 2007/0086633 A1    Apr. 19, 2007

(30) Foreign Application Priority Data

Sep. 23, 2005    (DE) ................ 10 2005 045 602

(51) Int. Cl.
*G06K 9/00* (2006.01)
*A61B 8/00* (2006.01)

(52) U.S. Cl. .................... 382/128; 600/443
(58) Field of Classification Search ......... 382/128–132, 382/154; 600/443
See application file for complete search history.

(56) References Cited

U.S. PATENT DOCUMENTS

| | | | |
|---|---|---|---|
| 5,313,567 A | | 5/1994 | Civanlar et al. |
| 5,836,872 A | * | 11/1998 | Kenet et al. .................. 600/306 |
| 6,336,899 B1 | * | 1/2002 | Yamazaki ................... 600/443 |
| 7,404,672 B2 | * | 7/2008 | Ostermeier ................. 378/205 |
| 2002/0058868 A1 | * | 5/2002 | Hoshino et al. ............. 600/423 |
| 2003/0135119 A1 | * | 7/2003 | Lee et al. .................... 600/461 |
| 2004/0161144 A1 | * | 8/2004 | Barth ......................... 382/154 |
| 2004/0223636 A1 | | 11/2004 | Edic et al. |
| 2005/0020878 A1 | * | 1/2005 | Ohnishi et al. ............. 600/117 |
| 2005/0090742 A1 | * | 4/2005 | Mine et al. ................. 600/443 |
| 2005/0197558 A1 | | 9/2005 | Williams et al. |
| 2006/0079745 A1 | * | 4/2006 | Viswanathan ............... 600/407 |

FOREIGN PATENT DOCUMENTS

| | | |
|---|---|---|
| DE | 100 83 899 T1 | 3/2002 |
| DE | 102 54 908 A1 | 6/2004 |
| EP | 1 466 552 A1 | 10/2004 |

* cited by examiner

*Primary Examiner*—Vu Le
*Assistant Examiner*—Amara Abdi

(57) ABSTRACT

With a method for supporting an interventional medical operation, a 3-dimensional image data set is recorded before the method. A positioning system is coupled with the coordinates system of the 3-dimensional image data set. The instrument is positioned and the position of the instrument in the 3-dimensional image data set is determined as an instrument image data point. Two further target image data points are determined in the target region, in which the instrument is to be guided. A plane is defined in this way. In this plane, the image data is used for a 2-dimensional display. Both the instrument image data point and also the two target image data points can be identified on the display, so that the target region of an interventional operation and an interventional medical device are displayed on an image at the same time. The image can be tracked during the interventional medical operation.

17 Claims, 1 Drawing Sheet

METHOD FOR SUPPORTING AN INTERVENTIONAL MEDICAL OPERATION

CROSS REFERENCE TO RELATED APPLICATIONS

This application claims priority of German application No. 10 2005 045 602.2 DE filed Sep. 23, 2005, which is incorporated by reference herein in its entirety.

FIELD OF INVENTION

The invention relates to a method for supporting an interventional medical operation based on a 3-dimensional image data set generated prior to the operation.

BACKGROUND OF THE INVENTION

The placing of catheters, biopsies (tissue removal) and TIPS (transingular intrahepatic portosystemic shunt, liver biopsy) form part of interventional medical operations. In these operations, 3-dimensional information of the most varied type is used, such information for instance being obtained on the basis of magnetic resonance imaging (MR), x-ray computed tomography (CT), 3D x-ray rotation angiography or by means of 3D ultrasound.

This 3-dimensional image information is used particularly with prior planning of interventional operations. The 3-dimensional image data serves here to provide information about the anatomy of the patient, for instance in order to clearly determine the location of a tumor in the body. With the actual implementation of the interventional operation, the 3-dimensional image information has until now been rarely used. A 2-dimensional imaging is generally carried out here with the aid of x-ray machines or electromagnetic classification systems (for instance the Biosense-Carto XP type).

It is also possible to display the 3-dimensional image data whilst carrying out the interventional operation. One possibility for this is the use of MPR layers (MPR stands for multiplanar reconstruction). In this way, the user selects, in a 3-dimensional image data set, the thickness and position of the layer to be displayed. The target region itself would be exclusively visible in such an image, i.e. the area of the anatomy of the patient body into which the instrument is to be introduced. In contrast, the instrument can be seen in the 2-dimensional x-ray images. A fused image is thus generated in the prior art, in which the instrument is shown at the same time, as well as the target region into which the instrument is to be introduced. The manual selection of the layer by the user renders the visualization of the 3-dimensional image data laborious, with simple tracking already not being possible, and the visualization must be continuously adjusted whilst the instrument is being guided. This involves a considerable expenditure of time during the interventional operation.

In the prior art, positioning systems are also used, for instance electrical positioning systems such as the Biosense Carto XP or positioning systems based on x-ray technology. These positioning systems however mainly provide the coordinates of the tips of the instrument, with the manner in which the information is displayed being selected by hand.

SUMMARY OF INVENTION

It is the object of the invention to extend the use of 3-dimensional image data during an interventional medical operation and to thereby better support the interventional medical operation.

The invention provides a method according to the claims in order to achieve the object.

The method according to the invention thus begins with the step in that a positioning system for a medical instrument used for the operation is coupled to the coordinates system of the 3-dimensional image data set. This is known as "registering" the 3D volume with the positioning system.

If the instrument is now positioned with the aid of the positioning system, an instrument image data point which characterizes the position of the instrument can be determined in the 3-dimensional image data set. The coupling of the positioning system with the 3-dimensional image data set thus allows the information relating to the coordinates of the instrument tips to be automatically passed to the image processing system and a point from the 3-dimensional image data set can be assigned to the instrument tip.

The next step involves determining at least one target image data point in the 3-dimensional image data set in a target region, into which the instrument is to be guided. A data selection which is suitable for the 2-dimensional display is subsequently determined from the 3-dimensional data set, with the data selection being defined and/or restricted with the aid of the instrument image data point and the target image data point.

Data selection is understood here to mean everything that can be displayed 2-dimensionally on the monitor with the aid of conventional reproduction methods. The prior art thus offers numerous methods here relating to how 3-dimensional data can be selected such that a 2-dimensional representation is enabled and is meaningful. Depending on the type of the data selection, it must be determined what is meant above by "being defined". Instrument and target image data points generally form part of the data selection, with two points already being sufficiently restricted such that many further steps are no longer required for the subsequent determination of the data selection.

The method according to the invention finally features the 2-dimensional display of the data selection on a monitor during the interventional operation.

Tracking is preferably carried out here, in particular in real time. In other words, the medical instrument is repeatedly positioned during its introduction into the target region, with an instrument image data point being repeatedly determined. With an unchanged target image data point, the steps used to determine the data selection and the 2-dimensional display of the data selection are repeated each time, with the steps of the method (with the exception of determining the target image data point) being repeated particularly in real time, whilst the medical instrument is being moved.

During the interventional medical operation, the 2-dimensional display which is dependent on the current location of the instrument and on the target region is repeatedly changed. It is thereby possible to display the target region and the location of the instrument to the user at the same time, so that even when the instrument is moved, it is possible to track how it is positioned relative to the target region, and with the selection from the 3-dimensional image data being illustrated here so that on the image it is possible to track whether the instrument can be moved undisturbed in the direction of the target region, or whether obstacles interfere with the path of the instrument.

With the invention, the target image data point is determined for instance in a similar manner to the previous planning of the interventional operation by means of the user him/herself. He can interactively directly determine the target image point (i.e. by actuating a user interface, such as a mouse for instance), i.e. by clicking on a corresponding point in the 3-dimensional image data set for instance, in order to define the target image data point. Aside from this direct determination (an input, an image data point), the target image data point can also be determined from a plurality of data values interactively input by the user. As the target image data point is intended to represent the target region, it can be necessary for the user to interactively determine a plurality of points which form part of the target region.

By way of example, the user can determine a surface which surrounds the target region. The center of gravity of the target region can then be calculated and determined as the target image data point. In this way, the surface need not necessarily completely surround the target region, methods for calculating the center of gravity can be used whereby the surface area of the target region is only determined on one side, assuming for instance a specific symmetry of the target region. It would be possible, for instance, to work with an idealized spherical shape.

Instead of inputting a complete surface, the user can also interactively determine a plurality of image data points, from which its center of gravity is identified and is then determined as the target image data point.

With a preferred embodiment of the invention, the data selection corresponds to a selection of a plane multiplanar reconstruction layer (MPR layer) from the 3-dimensional data set.

The use of a plane layer allows such a plane to be defined, which comprises the instrument image data point and the target image data point.

A further target image data point is preferably interactively determined. The plane passing through the instrument image data point and the two target image data points is then determined as a contour plane.

If the user does not input any further target image data points, a selection must be made between a plurality of planes in order to define the plane, in which planes in each case the straight line connection between an instrument image data point and a target image data point is contained. A plurality of planes are available to the user for selection, said planes to an extent representing different degrees of tilt, with the rotational axis being the straight line connection between the instrument image data point and target image data point during the tilt. To determine the contour plane, the user then selects one of the planes, by numerically inputting a tilt angle or by "scrolling" through the 3-dimensional image data set for instance.

With the above-mentioned preferred embodiment, in which the movement of the instrument is tracked, provision can hereby be made in that the tilt angle remains constant in each instance provided the user does not interactively determine a change in the tilt angle.

The method according to the invention can comprise the further step in that a second data selection is determined, which corresponds to a plane MPR layer perpendicular to the first MPR layer, which is likewise shown in a 2-dimensional view. Two layers arranged perpendicular to one another are thus displayed to the user. The orientation of the second plane can be determined such that a center of gravity of the two target image data points is determined half way between the first target data point and the further target data point, the center of gravity being connected to the instrument image data point and a second plane then being defined perpendicular to the first level, said second plane containing the connection from this center of gravity and the instrument image data point.

The present invention is not restricted to the use of plane multiplanar reconstruction layers. In particular, the data selection can correspond to the selection of a curved multiplanar reconstruction layer. The use of a curved multiplanar reconstruction layer is then particularly meaningful if the medical instrument itself has a curvature. This can be the case if body parts (organs) obstruct a straight insertion of the instrument during the intervention, so that a curved path of the instrument to the target region is predetermined by the curvature of the instrument. The curvature of the layer thus preferably corresponds to a curvature of the medical instrument. If the instrument image data point and the target image data point define the data selection such that they form parts of the curved layer, the curved MPR layer thus contains a path from the instrument image data point to the target image data point, which corresponds to a realistic future path of the instrument.

It was already mentioned above that the data selection, which is defined by the two image data points, can be any possible data selection which allows a 2-dimensional display of 3-dimensional image data. A completely different display is the "endoscopic view" for instance. The "endoscopic view" is a display in which the view of an endoscope is simulated. As the data selection with the present invention is preferably intended to be defined fully automatically on the basis of the two image data points, target image data point and instrument image data point, a display is defined as an "endoscopic view" if it starts from the instrument image data point and points and/or looks in the direction of the target image data point. With this display, the target image data point need not be identified itself, but can, to a certain extent, lie "behind" the display. The instrument image data point also need not be identified itself, the starting point is instead the perspective display.

The Maximum Intensity Projection display (MIP), the Shaded Surface Display (SSD) or the Volume Rendering Technique display (VRT) exist as further possible techniques for defining a data selection.

With the present invention, a 2-dimensional display is selected from the 3-dimensional image data fully automatically or on the basis of inputting a small amount of data. This is image data which has been recorded prior to the interventional operation. As in the prior art, x-ray recordings can still also be recorded during the interventional operation. The perspective thereof preferably corresponds to the 2-dimensional display. This above all relates to the use of plane MPR layers. In this case, it can be useful if the position of the C-arm of the x-ray device, on which the x-ray tube and the detector are mounted, are driven automatically such that the x-ray center beam of the x-ray system points perpendicularly to the 2-dimensional main layer illustrated on the monitor. In this case, the 2-dimensional x-ray image can be superimposed onto the illustrated layer of the 3-dimensional image data set. (To this end, only the x-ray system need be "registered" with the 3-dimensional data set, i.e. the coordinates systems are mutually coupled.) Overlaying symbols in the x-ray exposure or the combined display of x-ray exposure and MPR layer then allows the following to be visualized: the location of the instrument image data point, the location of the target image data point and/or the desired movement direction of the instrument. Finally, an arrow from the instrument image data point to the target image data point is preferably visualized.

BRIEF DESCRIPTION OF THE DRAWINGS

A preferred embodiment of the invention is now described with reference to the drawings, in which.

DETAILED DESCRIPTION OF INVENTION

Figure 1:
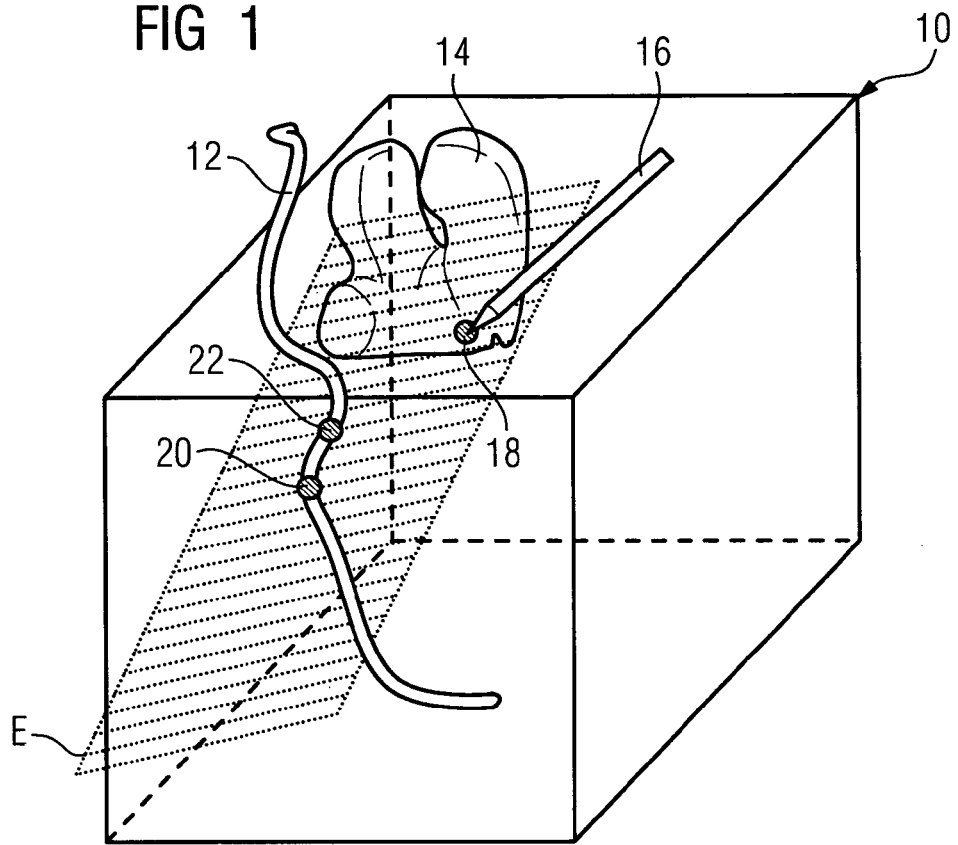
FIG. 1 shows a schematic representation of a volume, which represents a 3-dimensional image data set and illustrates how a layer is selected from this volume.

The boxes 10 shown in FIG. 1 represent a volume which is filled by a 3-dimensional image data set. A vessel 12 to be punctured as well as a further organ 14 are shown in the volume 10. Corresponding image data (points) in the 3-dimensional image data set are assigned to the vessel 12 and the organ 14.

During a puncture, the needle already inserted into the body is positioned with the aid of a positioning system. The needle is shown schematically in the volume 10 and is identified as 16. The needle tip is positioned. An instrument image data point 18 is determined in the 3-dimensional image data, said image data point 18 corresponding to the position of the needle 16.

A target image data point 20 as well as a further target image data point 22 are now interactively determined by a user who is viewing the 3-dimensional image data set. The two points 20 and 22 are selected in the target region into which the interventional instrument, namely the needle 16, is to be inserted. The present case concerns two regions of the vessel 12 to be punctured.

The three points 18, 20, 22 do not lie on a straight line, thereby enabling a plane E to be defined by means of these three points. This plane is now selected as a sectional plane for an MPR layer. In other words, image data points are taken out along this plane E from the 3-dimensional image data set and are displayed in a 2-dimensional manner.

Figure 2:
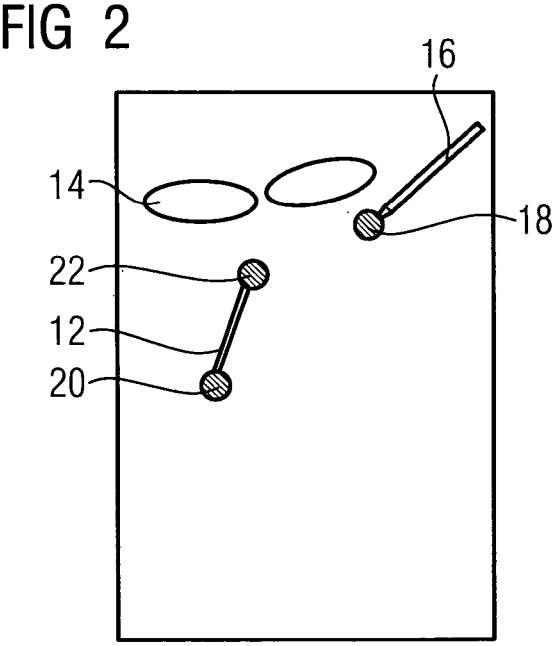
FIG. 2 shows a schematic representation of the display of the selected layer.

The 2-dimensional display of the image data point of plane E is shown in FIG. 2. On the one hand the display shows the anatomical parts of the patient which already exist in the 3-dimensional image data set, namely the vessel 12 to be punctured and the organ 14. Furthermore in accordance with the invention, the three points 18, 20, 22 are shown, namely the instrument image data point 18 on which the needle 16 can also be shown schematically (see FIG. 2) as well as the two target image data point 20 and 22.

For a user who has defined his target region by interactively inputting the target image data points 20 and 22, the display according to FIG. 2 is of outstanding use. Both the instrument tip 18 and also the target region, the section from the vessel 12, are shown in a single image. The user now knows how to guide the needle 16 so that the organ 14 is not damaged, and on the other hand, the target region, namely the vessel 12 to be punctured, is reached.

With the invention, the target region with the two target image data points 20 and 22 is determined once, the positioning of the point of the tip of the needle 16 is carried out several times. The display according to FIG. 2 can be regularly adjusted to the current position of the needle tip and the information from the 3-dimensional image data set is made available to the user in an optimal manner every time.

The invention is not predisposed to the interactive input of two target image data points 20 and 22. By way of example, only one individual target image data point 20 can be determined. The plane E to be defined then lies in a known manner such that it comprises the straight line from point 18 to point 20 and a plurality of possible planes corresponds to a rotation of planes about this straight line. The user can then view these planes and select a suitable orientation.

The target region is typically determined whilst the interactive operation is being planned. In the illustrated example, the target image data points 20 and 22 are thus determined prior to the actual intervention. The positioning of the needle tip of the instrument image data point 18 and the short-term determination of the plane E are carried out during the intervention.

The invention claimed is:

1. A method for supporting an interventional medical operation via a 3-dimensional image data set generated prior to the operation, comprising:
    coupling a positioning system for a medical instrument used for the operation with a coordinate system of the 3-dimensional image data set;
    positioning the instrument for the medical operation;
    determining an instrument image data point that identifies the instrument position in the 3-dimensional image data set;
    determining a target image data point in the 3-dimensional image data set in a target region into which the instrument is to be guided, wherein the user determines a surface which surrounds the target region, and the target image data point is the center of gravity of the target region;
    determining a contour plane from a plurality of planes available to a user, the plurality of planes including the instrument image data point and the target image data point, wherein each plane is defined by the instrument image data point, the target image data point and a respective degree of tilt about a rotation axis representing a straight line connection between the instrument image data point and the target image data point;
    selecting one of the pluralities of planes as the contour plane in response to the user inputting a numerical value for the respective tilt angle for said one plane;
    selecting a data selection suitable for a 2-dimensional display from the 3-dimensional data set via the instrument image data point and the target image data point, wherein the data selection consists of the selected contour plane;
    displaying the 2-dimensional display of the data selection on a monitor during the interventional operation; and
    registering an x-ray system with the 3-dimensional data set, wherein the x-ray system generates an x-ray exposure overlaid on the 2-dimensional display based on the selected contour plane wherein the x-ray exposure is recorded during the intervention operation wherein the x-ray exposure provides a visualization of:
    a position of the instrument image data point, or
    a position of the target image data point, or
    a movement direction of the instrument from the instrument image data point to the target image data point.

2. The method as claimed in claim 1, wherein the medical instrument is repeatedly positioned during the guidance into the target region.

3. The method as claimed in claim 2, wherein the instrument image data point is repeatedly determined.

4. The method as claimed in claim 3, wherein each time there is an unchanged target image data point the steps of selecting the data selection and displaying the 2-dimensional display are repeated.

5. The method as claimed in claim 4, wherein the steps of selecting the data selection and displaying the 2-dimensional display are repeated in real time during the guidance of the medical instrument.

6. The method as claimed in claim 1, wherein the target image data point is interactively directly determined by a user.

7. The method as claimed in claim 6, wherein the target image data point is determined from data values interactively input by a user.

8. The method as claimed in claim 7, wherein the user interactively determines a plurality of image data points from which a center of gravity thereof is defined and determined as the target image data point.

9. The method as claimed in claim 1, wherein the data selection corresponds to the selection of a plane multiplanar reconstruction layer from the 3-dimensional data set.

10. The method as claimed in claim 9, wherein a user interactively determines a further target image data point and a contour plane that passes through the instrument image data point.

11. The method as claimed in claim 10, wherein the target image data point and the further target image data points is the contour plane.

12. The method as claimed in claim 9, further comprising:
determining a second data selection that corresponds to a further plane multiplanar reconstruction layer and is arranged perpendicular to the first plane multiplanar reconstruction layer, and
displaying the second data selection 2-dimensionally.

13. The method as claimed in claim 1, wherein:
the data selection corresponds to a selection of a curved multiplanar reconstruction layer from the 3-dimensional data set, and
the curved multiplanar reconstruction corresponds to a curvature of the medical instrument.

14. The method as claimed in claim 1, wherein the data selection provides an endoscopic view starting from the instrument image data point in the direction of the target image data point.

15. The method as claimed in claim 1, wherein the data selection provides a Maximum Intensity Projection, a Shaded Surface Display, or a Volume Rendering Technique display.

16. The method as claimed in claim 1, wherein the x-ray exposure provides for a visualization by overlaying symbols of:
a position of the instrument image data point, and
a position of the target image data point, and
a movement direction of the instrument.

17. A method of providing a 2-dimensional display of data generated from a 3-dimensional image data set in order to support an interventional medical operation, comprising:
coupling a positioning system for a medical instrument used for the operation with a coordinate system of the 3-dimensional image data set that is generated prior to the medical operation;
positioning the instrument for the medical operation;
determining an instrument image data point that identifies the instrument position in the 3-dimensional image data set;
determining a target image data point in the 3-dimensional image data set in a target region into which the instrument is to be guided;
determining a contour plane from a plurality of planes available to a user, the plurality of planes including the instrument image data point and the target image data point, wherein each plane is defined by the instrument image data point, the target image data point and a respective degree of tilt about a rotation axis representing a straight line connection between the instrument image data point and the target image data point;
selecting one the plurality of planes as the contour plane in response to the user inputting a numerical value for the respective tilt angle for said one plane;
selecting a data selection suitable for a 2-dimensional display from the 3-dimensional data set via the instrument image data point and the target image data point, wherein the selection corresponds to multiplanar reconstruction layer from the 3-dimensional data set;
displaying the 2-dimensional display of the data selection on a monitor during the interventional operation; and
registering an x-ray system with the 3-dimensional data set, wherein the x-ray system generates an x-ray exposure having a center beam perpendicular to the multiplanar reconstruction layer, wherein the x-ray exposure is recorded during the intervention operation, wherein the x-ray exposure provides a visualization of:
a position of the instrument image data point, or
a position of the target image data point, or
a movement direction of the instrument from the instrument image data point to the target image data point.

* * * * *